United States Patent [19]

Twardowski et al.

[11] Patent Number: 4,687,471
[45] Date of Patent: Aug. 18, 1987

[54] PERITONEAL DIALYSIS CATHETER

[75] Inventors: Zbylut J. Twardowski; Karl D. Nolph; Ramesh Khanna, all of Columbia, Mo.

[73] Assignee: Curators of the University of Missouri, Columbia, Mo.

[21] Appl. No.: 826,823

[22] Filed: Feb. 6, 1986

Related U.S. Application Data

[63] Continuation-in-part of Ser. No. 729,185, May 1, 1985, abandoned.

[51] Int. Cl.⁴ ............................................. A61M 25/00
[52] U.S. Cl. ...................................... 604/175; 604/29; 604/280
[58] Field of Search ................. 604/175, 29, 280, 281, 604/264

[56] References Cited

U.S. PATENT DOCUMENTS

| | | |
|---|---|---|
| 4,184,497 | 1/1980 | Kolff et al. . |
| 4,392,855 | 7/1983 | Oreopoulos et al. ............... 604/175 |
| 4,437,856 | 3/1984 | Valli ....................................... 604/29 |
| 4,491,126 | 1/1985 | Cullor . |
| 4,496,349 | 1/1985 | Consentino ......................... 604/175 |

FOREIGN PATENT DOCUMENTS 0081724 6/1983 European Pat. Off. ............ 604/175
2552333 3/1985 France .

Primary Examiner—Stephen C. Pellegrino
Attorney, Agent, or Firm—Paul C. Flattery; Daniel D. Ryan

[57] ABSTRACT

A peritoneal catheter comprises a flexible catheter tube carrying porous cuff means to facilitate permanent securance of the catheter to the abdominal wall. The catheter tube defines, in its natural, unstressed condition, a bent segment adjacent the porous cuff means. This permits the catheter to be mounted in a tunnel formed through the abdominal wall in relatively unstressed configuration, with both ends pointing downwardly toward the feet of the patient. In one embodiment, the catheter includes a flange extending circumferentially outwardly of the catheter tube adjacent to the porous cuff means. The flange extends at a nonperpendicular angle relative to the axis of the catheter tube, and the slope of the flange extends transverse the direction of the bent segment. The angled flange, when sutured to the posterior rectus sheath, maintains the catheter tube in the desired tunnel direction within the abdominal wall, with the distal end of the catheter tube pointed properly downwardly toward the pelvic cavity.

11 Claims, 7 Drawing Figures

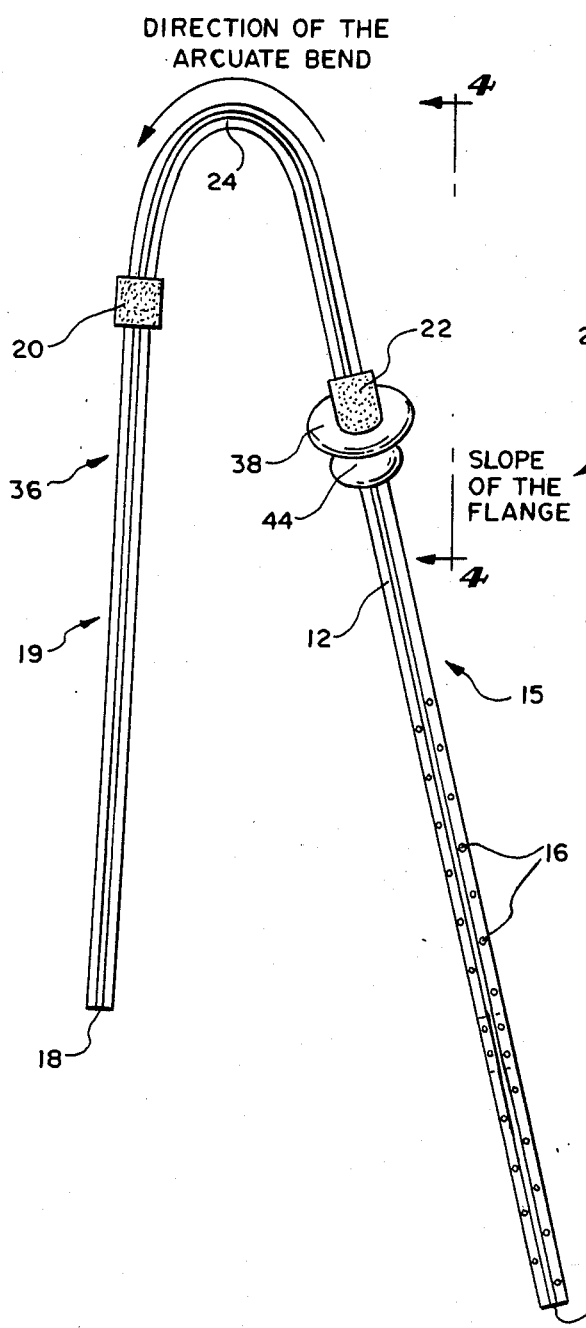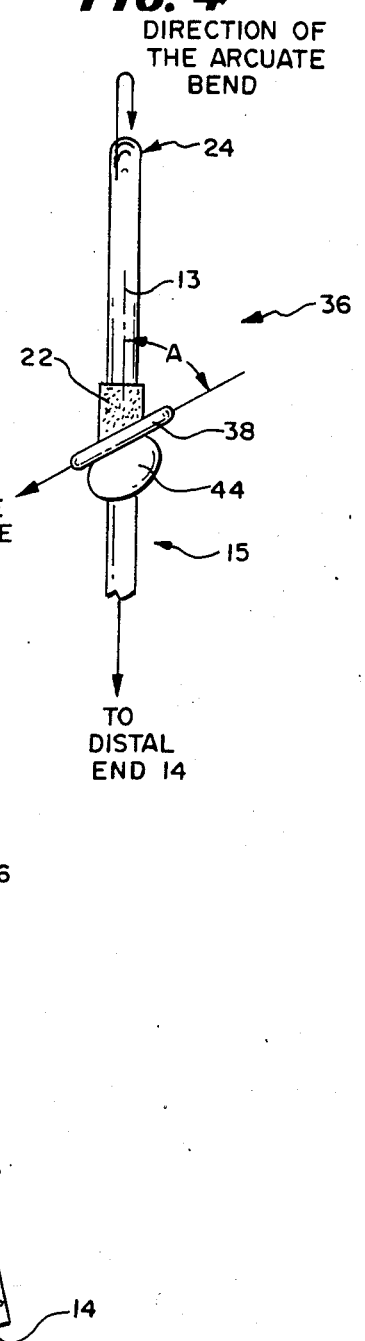

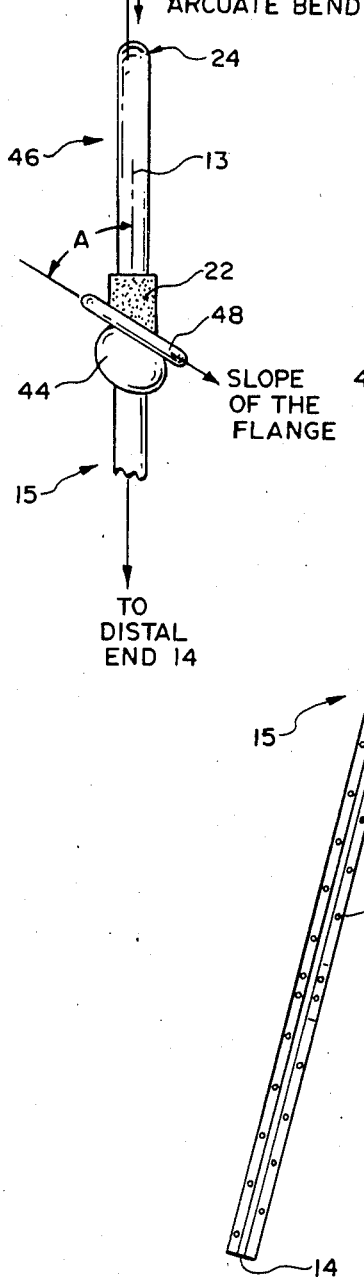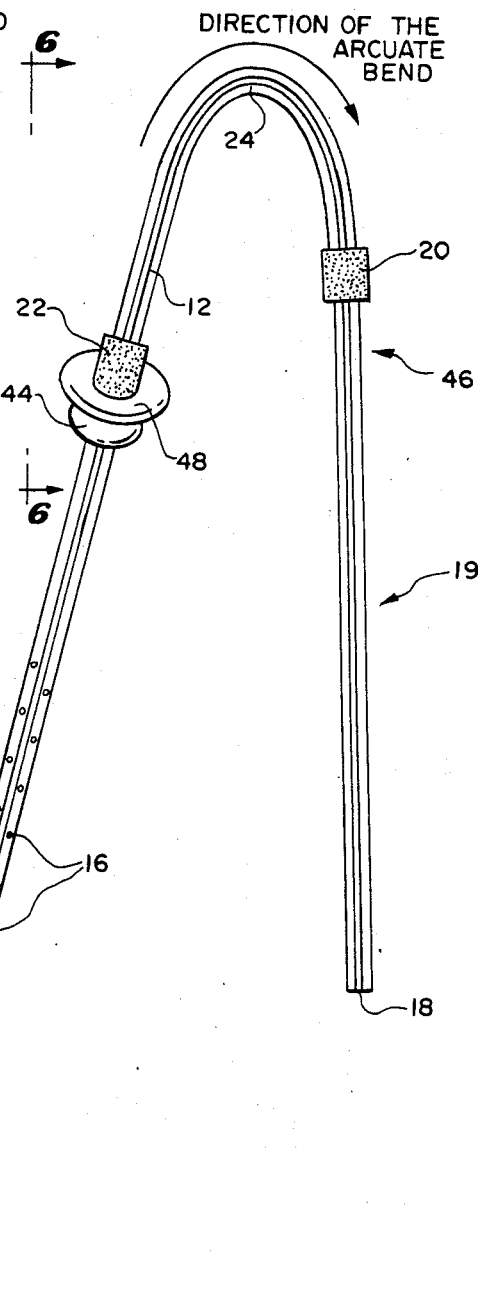

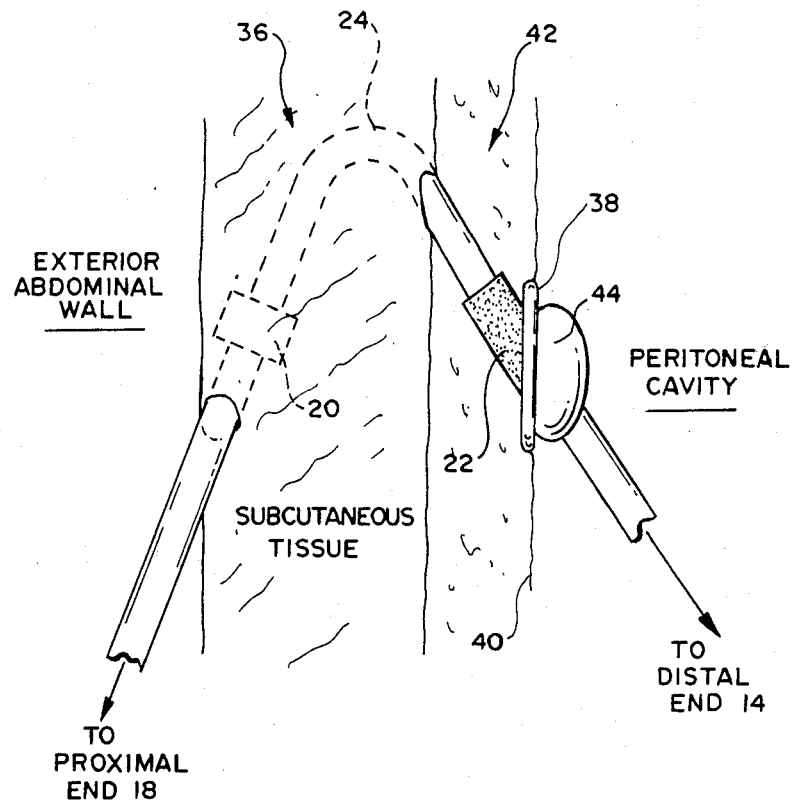

PERITONEAL DIALYSIS CATHETER

RELATED APPLICATION

This application is a continuation-in-part of Twardowski et al U.S. application Ser. No. 729,185, filed May 1, 1985 now abandoned.

TECHNICAL FIELD

The Tenckhoff catheter is commercially available and widely used with patients who must undergo chronic peritoneal dialysis for maintenance in the absence of normal kidney function. The catheter is made of silicone rubber, and has a pair of porous tissue attachment cuffs in spaced relation to each other, so that after implantation of the catheter into the abdominal wall, tissue grows into pores of the cuffs, for secure and permanent anchoring of the catheter in place. In the article by Tenckhoff and Schechter entitled "A Bacteriologically Safe Peritoneal Access Device," Trans. Am. Soc. Artif. Intern. Organs 1968; 14:181-187, the authors disclosed their new catheter and showed an arcuate subcutaneous catheter tunnel, so that both the external and internal end segments of the catheter were generally directed in a caudal direction (i.e., downwardly, toward the feet of the patient).

In the practice of installation of such peritoneal catheters, this technique is often followed, so that both the outer end of the catheter outside of the body and lying over the skin, and the inner end of the catheter within the peritoneal cavity, typically point downwardly toward the pelvis or feet.

However, known peritoneal catheters have been molded and cured in generally straight configuration, so that their natural, unstressed configuration is a straight line, although the catheters are flexible and may be placed in other configurations. Accordingly, peritoneal catheters of the prior art must be stressed by bending into a substantially U-shape, in order to be installed into a curved tunnel through the abdominal wall, which holds the catheter in its downward facing, U-shaped position so that both ends of the catheter extend downwardly.

Significant advantages have been found for this arrangement. For example, in currently unpublished data by authors including us, it has been statistically shown that patients who have downwardly caudally pointing outer ends of their peritoneal catheter have fewer days of catheter tunnel infection, when compared with patients whose catheter ends point either upwardly or in a sideward direction.

Currently, however, disadvantages of this arrangement also exist. First, it appears that the elastic memory of the catheter, which urges it to assume its original, unstressed, straight configuration, can cause catheter cuffs to be expelled from the tunnel site in a slow, migratory process. This of course is most disadvantageous. Secondly, the inner end portion of the catheter can migrate upwardly with greater ease, due to the internal stresses of the catheter tending to urge it straight. It is undesirable for the catheter to migrate upwardly to upper portions of the peritoneal cavity, where it is prone to omental wrapping and one way obstruction of flow through the catheter. Accordingly, there is a need to keep the inner catheter portion positioned in the lower portions of the peritoneal cavity, adjacent the pelvis. There is also a need to maintain the desired tunnel direction of the catheter within the abdominal wall.

In accordance with this invention, the above disadvantages are reduced by the use of a modified catheter.

DESCRIPTION OF THE INVENTION

In one aspect of this invention, a peritoneal catheter comprises a flexible catheter tube, which may be made of silicone rubber or equivalent material. The tube has a proximal and a distal end portion. The distal end portion defines flow port means for fluid communication between the bore of the catheter tube and the peritoneal cavity. The catheter also carries porous cuff means to facilitate permanent securance of the catheter to the abdominal wall.

In accordance with this aspect of the invention, the catheter tube defines, in its natural, unstressed condition, a bent segment adjacent the porous cuff means. As the result of this, the catheter can be mounted in a tunnel formed through the abdominal wall in relatively unstressed condition, with the bent segment being mounted in the tunnel. Hence, the proximal end portion of the catheter may extend outwardly from the abdominal wall and downwardly from the outer end of the tunnel, while the distal end portion of the catheter extends inwardly and downwardly from the inner end of the tunnel into the peritoneal cavity.

Because of the unstressed bent segment, the catheter of this invention occupies the desired position where both ends thereof point caudally or downwardly, while at the same time the catheter tube is in relatively natural, unstressed condition, when compared with prior art catheters which have been placed in such a position. Thus, less urging force is present in the catheter to cause gradual expulsion of cuffs from the tunnel formed in the abdominal wall. Also, less force is present urging the distal end portion of the catheter upwardly out of its desired position in a lower portion of the peritoneal cavity.

Additionally, the installed catheter of this aspect of invention can exhibit significantly reduced days of tunnel infection which the patient must endure, because of the downward pointing aspect of the proximal end portion of the catheter. It is believed that downwardly pointing proximal end portions of peritoneal catheters permit improved draining from the tunnel area in the event of an infection, which can significantly reduce the severity of the infection. Also, less contamination of the tunnel site takes place because of the migration of sweat and bacteria-laden water into the tunnel area, because its outer end points downwardly along with the proximal end portion of the catheter.

It is generally preferred for the bent segment of the catheter to define an arc of 90° to 180° so that the proximal and distal end portions form an angle to each other that is supplementary to the angle of said arc. A "supplementary" angle is an angle which, when combined with the arc angle, totals 180°. Accordingly, if the arc of the bent segment is 120°, the proximal and distal end portions will form an angle with each other of 60°. Most preferably, the bent segment defines an arc of about 120° to 170°.

The use of a bent segment which defines an arc makes possible the formation of a substantial angle in the catheter, as shown in the drawings, without the danger of kinking of the catheter, as might take place if a merely angled corner were used rather than an arc.

The porous cuff means on the catheter may be any conventional cuff used for tissue attachment to a catheter. While a single, porous cuff may be used, it is preferable to use a pair of spaced, porous cuffs in the manner of the well-known Tenckhoff catheter as it is currently commercially available. One cuff, hereafter called the exterior cuff, attaches to the subcutaneous tissue near the exterior abdominal wall. The other cuff, hereafter called the interior cuff attaches within the rectus muscle near the posterior rectus sheath. The bent segment of the catheter, as above described, is positioned between the interior and exterior cuffs.

In another aspect of the invention, an outwardly extending flange circumferentially surrounds the catheter just below the interior cuff. The flange extends in a nonperpendicular relationship relative to the axis of the catheter tube, being slanted at an angle less than 90° relative to the axis of the catheter. When viewed in the direction of the arcuate bend in the catheter, the direction of the slope extends generally transverse the direction of the arcuate bend. Preferably, the angle of the slope is between about 30° and 50°, with the most preferred angle being about 45°.

The direction of the slope of the flange maintains the desired direction of the catheter inside the tunnel formed within the abdominal wall. When the flange is sloped upwardly to the right, as viewed from the distal end leg of the catheter in the direction of the arcuate bend, the catheter is intended to maintain a right tunnel implacement, as described in more detail below. When the flange is sloped upwardly to the left, as viewed from the same perspective the catheter is intended to maintain a left tunnel implacement, also as described in more detail below.

When the angled flange is sutured flat against the posterior rectus sheath, the desired tunnel direction of the catheter is maintained within the abdominal wall, with the distal end of the catheter pointing in the desired caudal direction within the peritoneal cavity.

DESCRIPTION OF THE DRAWINGS

FIG. 3 is a plan view of another embodiment of the catheter of this invention, showing the catheter having an angled flange adjacent to the interior cuff, the catheter being intended for "right tunnel" implacement;

FIG. 4 is a side view of the angled flange of the catheter taken generally along line 4—4 in FIG. 3;

FIG. 5 is a plan view of another embodiment of the catheter of this invention, showing the catheter having an angled flange adjacent to the interior cuff, the catheter being intended for "left tunnel" implacement;

FIG. 6 is a side view of the angled flange of the catheter taken generally along line 6—6 in FIG. 5; and FIG. 7 is a generally schematic side section view of the catheter shown in FIG. 3 implaced within the peritoneal cavity of a patient.

DESCRIPTION OF SPECIFIC EMBODIMENTS

Figure 1:
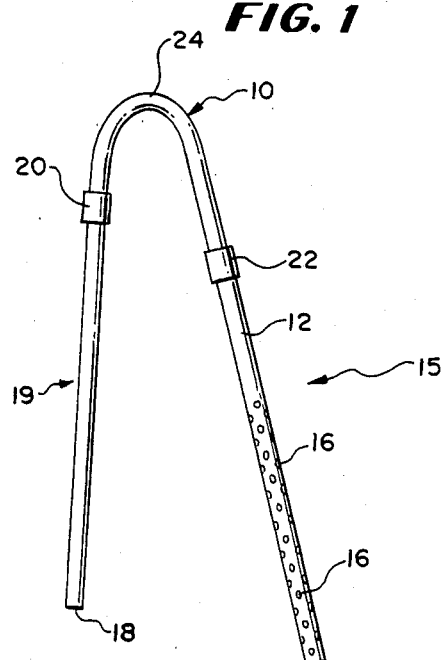
FIG. 1 is a plan view of one embodiment of the catheter of this invention in its natural, unstressed configuration.

Referring to the drawings, catheter 10 is a peritoneal catheter generally of the design of a commercially available Tenckhoff catheter, except as otherwise described herein. Catheter 10 comprises a flexible catheter tube 12 which may be made of silicone rubber or any other desired and appropriate material. Adjacent the distal end 14 of the catheter, a plurality of flow ports 16 are formed in the wall of the catheter, while distal end 14 itself may be open as well, for added flow communication between the exterior and the bore of catheter 10.

Proximal end 18 defines an open bore as well for receiving typically a titanium adaptor of known design, to provide connection with a transfer set or other means for flow communication with peritoneal dialysis solution containers.

A pair of cuffs 20, 22 of known designs are also provided. Outer cuff 20 is intended to be positioned within the abdominal wall tunnel within the subcutaneous tissue about 2 centimeters from the outer skin. Cuff 22 is intended to be positioned adjacent the inner end of the abdominal tunnel, near the posterior rectus sheath. The abdominal tunnel may be formed by the surgeon when the catheter is installed in the patient's abdomen.

In accordance with this invention, catheter 10 defines in its natural, unstressed condition, a bent segment 24. As shown, bent segment 24 defines an arc which may most preferably extend on the order of 150°-170°. A catheter may be manufactured with such an unstressed bend by molding the catheter, or causing it to be cross-linked, while in the desired bent position. The bent segment 24 effectively forms two legs 15 and 19 in the catheter 10, one leg 15 associated with the distal end 14, and the other leg 19 associated with the proximal end 18.

Figure 2:
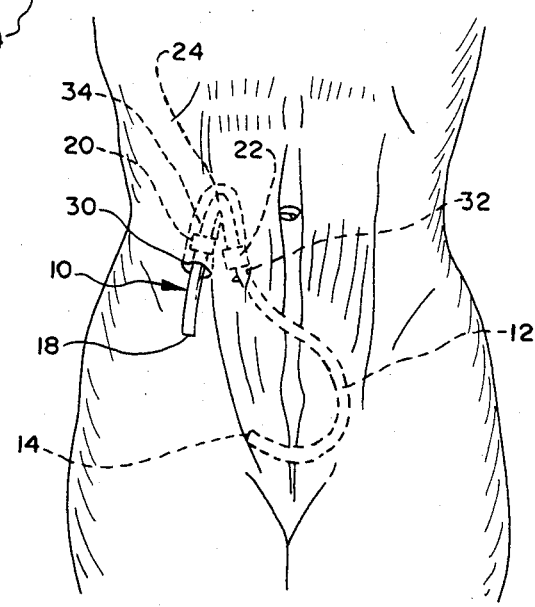
FIG. 2 is a generally schematic view of the catheter of FIG. 1 as it may preferably be installed in the peritoneal cavity of a patient.

FIG. 2 illustrates how the catheter may be installed in the peritoneal cavity of the patient, with proximal end 18 projecting outwardly from the outer end 30 of the tunnel 34 formed by the surgeon in the abdominal wall. Distal end 14 of the catheter projects downwardly from the inner end 32 of the tunnel formed by the surgeon. Accordingly, since bent segment 24 is not as stressed as the catheters of prior art, there is less urging force to cause the distal end portion of the catheter to migrate upwardly in the peritoneal cavity.

It is generally preferable for tunnel 34 to be formed on one side of the patient, spaced from the midline of said patient. Also, proximal end 18 may be positioned at a small angle to the midline of the patient. In FIG. 2, the tunnel 34 is angled so that the exposed proximal end 18 is positioned, when viewed by an on-looker, slightly to the left and pointed downwardly. This is called a "right tunnel" implacement.

Alternately (not shown), the tunnel may be angled so that the exposed end 18 is positioned, when viewed by an on-looker, slightly to the right and pointed downwardly. This is called a "left tunnel" implacement.

A statistical analysis of the frequency and severity of infections made by a group, including us, has found that downward external tunnel implacement left or right provides the lowest number of days of tunnel infection that a patient must endure, when compared with any other position of tunnel 34. More particularly, we found that four catheters, installed in patients for a total of 2,136 days, in which the outer portions of the tunnels 34 extended in a direction no more than 45° away from straight down in the standing patient, resulted in no tunnel exit site infection at all. For catheter installations having higher angles than this from the straight down direction, increasing difficulties with tunnel site infection were encountered, which grew progressively worse as the angle grew larger, and was worst of all when the tunnel site exit pointed generally upwardly.

FIG. 2 shows an ideal placement of the catheter of this invention in the abdomen.

In FIG. 3, another peritoneal catheter 36 is shown which embodies the features of the invention. The catheter 36 is constructed generally like the catheter 10 shown in FIG. 1, having distal and proximal ends 14 and 18 and an intermediate bent section 24. Other structural elements which are common to FIG. 1 are also given the same reference numerals as in FIG. 1.

The catheter 36 shown in FIG. 3 differs from the catheter 10 shown in FIG. 1 by the inclusion of a flange 38 which is located adjacent to and directly below the internal cuff 22. The flange 38 is intended to be sutured to the posterior sheath 40 of the rectus muscle 42, as shown in FIG. 7.

A bead 44 is provided below the flange 38. The bead 44 extends within the peritoneal cavity (again, see FIG. 7) on the side of the posterior rectus sheath 40 opposite to the flange 38.

In accordance with the invention, the flange 38 is angled in a nonperpendicular relationship relative to the axis 13 of the catheter 36. As shown in FIG. 4, the angle (designated A in FIG. 4), measured between the axis 13 and the flange 38, is generally between about 30° and about 50°. As is also shown in FIG. 4, the slope of the flange 38, when viewed in side section in the direction of the arcuate bend 24 from the distal end leg 15 of the catheter 36, extends in a direction transverse the direction of the bend 24 of the catheter 36.

In FIG. 4, the flange 38 is shown angled sloping upwardly to the right, when viewed from the distal end leg 15 in the direction of the arcuate bend 24. In this arrangement, the catheter 36 is intended for right tunnel implacement, with the exposed proximal end 18 of the catheter 36 angled slightly to the right and pointed downwardly, when viewed by an on-looker, as shown in FIG. 7.

Another catheter 46 is shown in FIGS. 5 and 6. This catheter 46, like catheter 36, has an angled flange 48. The catheter 46 is identical to the catheter 36 (shown in FIGS. 3 and 4), except that the flange 48, when viewed from the distal end leg 15 of the catheter 46 in the direction of the arcuate bend 24, is angled sloping upwardly to the left, as shown in FIG. 6. In this arrangement, the catheter 46 is intended for left tunnel implacement, with the exposed proximal end 18 of the catheter angled slightly to the left and pointed downwardly, as is shown in FIG. 2.

When sutured flat against the posterior rectus sheath 40, as shown in FIG. 7, the angled flange 38 or 48 maintains the desired right or left tunnel direction within the abdominal wall. Furthermore, the flange 38 or 48 maintains the distal end 14 of the catheter pointing in the desired caudal direction within the peritoneal cavity. The flange 38 or 48, coupled with the arcuate bend 24 of the catheter 36 or 46, prevents migration of the catheter during use, maintaining the catheter in the optimal relationship within the peritoneal cavity. Tunnel infection is thereby reduced, and overall patient comfort improved.

The above has been offered for illustrative purposes only, and is not intended to limit the scope of the invention of this application, which is as defined in the claims below.

We claim:

1. A peritoneal catheter which comprises a flexible catheter tube having a proximal end portion which, in use, projects outwardly from the abdominal cavity of a patient and a distal end portion which, in use, projects inwardly into the peritoneal cavity of the patient, the improvement comprising:

said catheter tube defining in its natural, unstressed condition, a bent segment between the proximal end portion and the distal end portion, said bent segment, in use, extending through the subcutaneous tissue and rectus muscle of the abdominal wall, through the posterior rectus sheath and into the peritoneal cavity.

and further including a flange circumferentially surrounding said catheter tube, said flange extending at a nonperpendicular angle relative to the axis of said catheter tube and, in use, secured against the posterior rectus sheath of the patient, the slope of said flange extending in a direction transverse the direction of said bent segment to maintain the distal end portion pointed in a caudal direction within the peritoneal cavity of the patient while the proximal end projects, when viewed by an on-looker, downwardly and at an angle relative to the midline of the patient.

2. A catheter according to claim 1 wherein said angle of said flange is about 30° to about 50° measured from the axis of said catheter tube.

3. A catheter according to claim 2 wherein said angle is about 45°.

4. A peritoneal catheter according to claim 1 wherein said slope of said flange maintains the proximal end of the catheter, when viewed by an on-looker, projected downwardly and angled to the left relative to the midline of the patient.

5. A peritoneal catheter according to claim 1 wherein said slope of said flange maintains the proximal end of the catheter, when viewed by an on-looker, projected downwardly and angled to the right relative to the midline of the patient.

6. A peritoneal catheter according to claim 1 and further including a porous cuff on the catheter tube adjacent to said flange, said cuff, in use, positioned within the rectus muscle of the patient, near the posterior rectus sheath.

7. A peritoneal catheter comprising
a flexible catheter tube having a proximal distal end portion and a distal end portion,
an exterior porous cuff positioned on said flexible catheter tube near said proximal distal end portion,
an interior porous cuff position on said flexible catheter spaced away from said exterior porous cuff toward said distal end portion,
said catheter tube defining in its natural unstressed condition, a bent segment between said exterior and interior porous cuffs, and
a flange circumferentially surrounding said catheter tube adjacent to said interior porous cuff, said flange extending at a nonperpendicular angle relative to the axis of said catheter tube, the slope of said flange extending in a direction transverse the direction of said bent segment.

8. A peritoneal catheter according to claim 7 wherein said angle of said flange is about 30° to about 50° measured from the axis of said catheter tube.

9. A peritoneal catheter according to claim 8 wherein said angle is about 45°.

10. A peritoneal catheter according to claim 1 or 2 or 3 or 7 or 8 or 9 wherein said bent segment defines an arc of about 90° to about 180° so that the proximal and distal end portions form an angle to each other that is supplementary thereto.

11. A peritoneal catheter according to claim 10 in which said bent segment defines an arc of about 120° to about 170°.

* * * * *